(12) United States Patent
Isawa et al.

(10) Patent No.: US 8,003,694 B2
(45) Date of Patent: Aug. 23, 2011

(54) CRYSTAL OF HYDROXYNOREPHEDRIN DERIVATIVE HYDROCHLORIDE ¼ HYDRATE

(75) Inventors: Hidetoshi Isawa, Joetsu (JP); Michio Toda, Matsumoto (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 237 days.

(21) Appl. No.: 11/912,420

(22) PCT Filed: Apr. 24, 2006

(86) PCT No.: PCT/JP2006/308591
§ 371 (c)(1),
(2), (4) Date: Oct. 24, 2007

(87) PCT Pub. No.: WO2006/118087
PCT Pub. Date: Nov. 9, 2006

(65) Prior Publication Data
US 2009/0036526 A1    Feb. 5, 2009

(30) Foreign Application Priority Data
Apr. 26, 2005  (JP) .................................. 2005-128731

(51) Int. Cl.
*A61K 31/24* (2006.01)
*C07C 229/38* (2006.01)

(52) U.S. Cl. ......................................... 514/534; 560/42

(58) Field of Classification Search ................... 514/534; 560/42
See application file for complete search history.

(56) References Cited

U.S. PATENT DOCUMENTS
2004/0229947 A1  11/2004  Yamazaki et al.
2004/0242686 A1  12/2004  Isawa et al.
2006/0135605 A1   6/2006  Tanaka et al.

FOREIGN PATENT DOCUMENTS
EP    1095932 A1   5/2001
EP    1426355 A1   9/2004
EP    1 535 897 A1  1/2005
JP    2002-338513 A  11/2002
WO    03/024916 A1   3/2003

OTHER PUBLICATIONS
Supplementary European Search Report dated Jun. 30, 2010.

*Primary Examiner* — Sreeni Padmanabhan
*Assistant Examiner* — Sahar Javanmard
(74) *Attorney, Agent, or Firm* — Sughrue Mion, PLLC

(57) ABSTRACT

The present invention provides ethyl (−)-2-[4-[2-[[1S,2R]-2-hydroxy-2-(4-hydroxyphenyl)-1-methylethyl]amino]ethyl]-2,5-dimethylphenoxyacetate hydrochloride ¼ hydrate or a crystal thereof which can be determined by characteristic diffraction peaks of the powder X-ray diffraction, thermogravimetry-differential thermal analysis or the like, and obtained by manufacturing ethyl (−)-2-[4-[2-[[1S,2R]-2-hydroxy-2-(4-hydroxyphenyl)-1-methyl-ethyl]amino]ethyl]-2,5-dimethylphenoxyacetate by a specific method.

3 Claims, 6 Drawing Sheets

CRYSTAL OF HYDROXYNOREPHEDRIN DERIVATIVE HYDROCHLORIDE ¼ HYDRATE

CROSS REFERENCE TO RELATED APPLICATIONS

This application is a National Stage of International Application No. PCT/JP2006/308591 filed on Apr. 24, 2006, claiming priority based on Japanese Patent Application No. 2005-128731, filed Apr. 26, 2005, the contents of all of which are incorporated herein by reference in their entirely.

TECHNICAL FIELD

The present invention relates to novel ethyl (−)-2-[4-[2-[[1S,2R]-2-hydroxy-2-(4-hydroxyphenyl)-1-methylethyl]amino]-ethyl]-2,5-dimethylphenoxyacetate hydrochloride ¼ hydrate represented by the following formula (I):

[Chem. 1]

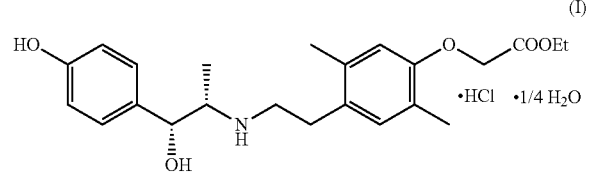

(I)

or especially crystals thereof, which have a $\beta_3$-adrenaline receptor stimulating effect and is useful as an agent for treating pollakiuria or urinary incontinence.

BACKGROUND ART

Ethyl (−)-2-[4-[2-[[1S,2R]-2-hydroxy-2-(4-hydroxyphenyl)-1-methylethyl]amino]ethyl]-2,5-dimethylphenoxyacetate represented by the following formula (II):

[Chem. 2]

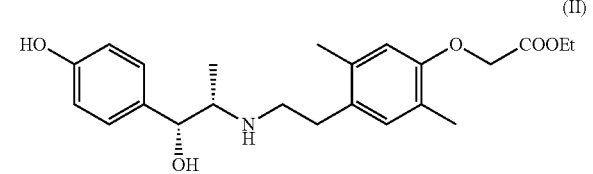

(II)

has an excellent $\beta_3$-adrenaline receptor stimulating effect and is a useful compound as a therapeutic agent for pollakiuria or urinary incontinence (see Patent Reference 1).

Heretofore, a crystalline hydroxynorephedrine derivative hydrochloride represented by the following formula (III):

[Chem. 3]

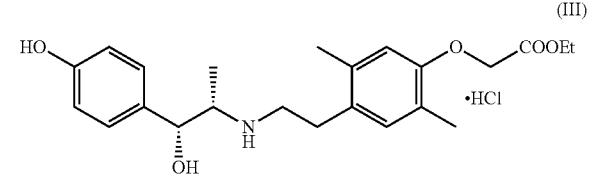

(III)

and a crystal polymorph thereof have been reported in Patent Reference 2 as a hydroxynorephedrine derivative hydrochloride represented by the above formula (II).

More particularly, crystals represented by the above formula (III) wherein the diffraction pattern by the powder X-ray diffractometry shows characteristic peaks at diffraction angles (2θ) of 8.9, 10.2, 12.9, 14.2, 15.6, 18.4 and 20.6 (crystalline form A) and the diffraction pattern by the powder X-ray diffractometry shows characteristic peaks at diffraction angles (2θ) of 7.3, 10.1, 12.2, 14.6, 15.9, 16.0, 18.7 and 21.8 (crystalline form B) have been reported. However, a hydrate of the hydroxynorephedrine derivative hydrochloride represented by the above formula (I) has not been reported so far.

Patent reference 1: International Publication No. WO00/02846 pamphlet

Patent reference 2: International Publication No. WO03/024916 pamphlet

DISCLOSURE OF THE INVENTION

Objects to be Solved by the Invention

Usually, in a compound which has crystal polymorphs, each crystal polymorph has a different property in various ways, and even if it is the same compound, it may show a different interaction effect. Especially, in case of a medicine, it is known that if there are differences in solubility, dissolution rate and the like, bioavailabilities of the medicine are also different. Therefore, newly finding a new crystal polymorph with a different solubility leads to providing a new opportunity to improve the performance characteristic of the medicine, for example, making it possible to widen materials for a pharmaceutical researcher to design the dosage form of the medicine having a desired characteristic.

In addition, a compound which has crystal polymorphs is used as a medicine, a stable supply of the compound having the constant crystal polymorph is required so that constant interaction effects can be always expected. For getting consistent quality and constant interaction effect needed as medicines, it is desired earnestly to establish a stably manufacturing method to get a compound having the constant crystal polymorph.

Therefore, the object of the present invention is to provide a novel crystal polymorph of a compound derived from a hydroxynorephedrine derivative represented by the above formula (II) and a manufacturing method therefor.

Means of Solving the Problems

In order to solve the aforementioned problems, as a result the present inventors have studied earnestly on the hydroxynorephedrine derivative represented by the above formula (II), they newly found ethyl (−)-2-[4-[2-[[1S,2R]-2-hydroxy-2-(4-hydroxyphenyl)-1-methylethyl]amino]ethyl]-2,5-dimethylphenoxyacetate hydrochloride ¼ hydrate (hereinafter referred to as crystalline form F) and ethyl (−)-2-[4-[2-[[1S,2R]-2-hydroxy-2-(4-hydroxyphenyl)-1-methylethyl]amino]ethyl]-2,5-dimethylphenoxyacetate hydrochloride ½ tetrahydrofuran solvate (hereinafter referred to as crystalline form G), and they acquired the knowledge that these crystal polymorphs can be prepared with constant quality according to the method mentioned later, and furthermore, crystal form F has an excellent water-solubility and is extremely useful as a medicine, thereby forming the bases of the present invention.

That is, the present invention relates to ethyl (−)-2-[4-[2-[[1S,2R]-2-hydroxy-2-(4-hydroxyphenyl)-1-methylethyl]amino]-ethyl]-2,5-dimethylphenoxyacetate hydrochloride ¼ hydrate represented by the following formula (I):

[Chem. 3]

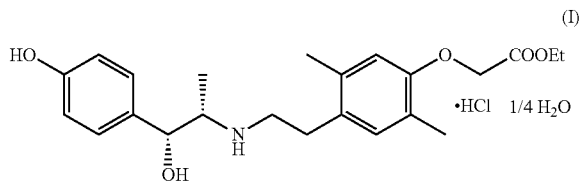

(I) ·HCl 1/4 H₂O or especially a crystal wherein the diffraction pattern by the powder X-ray diffractometry has characteristic peaks at diffraction angles (2θ) of 6.5, 11.7, 13.0, 14.0, 16.4, 18.6 and 21.6.

Ethyl (−)-2-[4-[2-[[1S,2R]-2-hydroxy-2-(4-hydroxyphenyl)-1-methylethyl]amino]ethyl]-2,5-dimethylphenoxyacetate hydrochloride ¼ hydrate represented by the above formula (I) of the present invention and crystalline form F that is a specific crystal polymorph thereof can be prepared in the following way.

That is, ethyl (−)-2-[4-[2-[[(1S,2R)-2-hydroxy-2-(4-hydroxyphenyl)-1-methylethyl]amino]ethyl]-2,5-dimethylphenoxy]acetate prepared by the method described in Patent reference 1 is dissolved by adding 2 to 5 times the amount of toluene. About 1 equivalent of 30 weight % hydrogen chloride solution in ethanol is added to the solution under ice-cooling, and the reaction mixture is stirred for 1 to 3 hours at 10 to 30° C. The precipitated crystals are collected, and dried under reduced pressure at about 60° C. By storing the obtained crystals under an atmosphere of a temperature between 20 to 30° C. and a relative humidity between 50 to 70% for one night or more, crystalline form F of ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride ¼ hydrate can be prepared.

In this way, for preparing crystalline form F, after ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride prepared by the manufacturing method described in Patent reference 1 is crystallized and dried under the above special condition, it is important to store crystalline form F under specific condition of a temperature between 20 to 30° C. and a relative humidity between 50 to 70%. For example, ethyl (−)-2-[4-[2-[[(1S,2R)-2-hydroxy-2-(4-hydroxyphenyl)-1-methylethyl]amino]ethyl]-2,5-dimethylphenoxy]acetate prepared only by the method described in Example 1 of Patent reference 2 is not a hydrate or crystalline form F.

In addition, ethyl (−)-2-[4-[2-[[1S,2R]-2-hydroxy-2-(4-hydroxyphenyl)-1-methylethyl]amino]ethyl]-2,5-dimethylphenoxyacetate hydrochloride ½ tetrahydrofuran solvate and crystalline form G that is a specific crystal polymorph thereof can be prepared in the following way.

Ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride prepared by the manufacturing method of Example 7 described in International Publication WO2004/026807 pamphlet is dissolved by heating in a mixed solvent of 1 to 2 times the amount of methanol and 15 to 60 times the amount of tetrahydrofuran. At this time, 15 to 30 times the amount of tetrahydrofuran may be added. And then about 20 to 70% of the total amount of the solvent used is removed under the normal pressure. The residue is cooled for 30 minutes to 12 hours under ice-cooling to at room temperature, and the precipitated crystals are collected and dried under reduced pressure at room temperature to obtain crystalline form G of ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride ½ tetrahydrofuran solvate.

Crystalline forms F and G obtained can be identified by the following characteristic diffraction peaks as shown in the powder X-ray diffraction charts of FIGS. 1 and 2.

That is, (1) Crystalline form F has characteristic peaks at diffraction angles (2θ) of 6.5, 11.7, 13.0, 14.0, 16.4, 18.6 and 21.6 degrees as shown in FIG. 1.

(2) Crystalline form G has characteristic peaks at diffraction angles (2θ) of 6.3, 11.9, 12.6, 17.0, 19.0, 20.9 and 22.2 degrees as shown in FIG. 2.

In addition, the crystal polymorph can also be discriminated by thermogravimetry-differential thermal analysis (TG/DTA) or solid state $^{13}C$-NMR spectrum. Each data of the thermogravimetry-differential thermal analysis (TG/DTA) are shown in FIGS. 3 and 4, and each data of the solid state $^{13}C$-NMR spectrum are shown in FIGS. 5 and 6.

Since crystalline form F of the present invention does not cause polymorphic transformation during the storage under usual conditions (25° C. and 60% relative humidity) and has an excellent chemical stability during storage, and the quality can be maintained constantly, crystalline form F can be provided as medicinal bulks. In addition, since crystalline form F has an excellent water-solubility, it is suitable as medicines.

Crystalline form F of the present invention exhibits an excellent $β_3$-adrenoceptor stimulating effect and relaxes bladder detrusor muscle and increases the volume of bladder. Therefore, crystalline form F can be used for the treatment of dysuria such as pollakiuria or urinary incontinence in nervous pollakuria, neurogenic bladder dysfunction, nocturia, unstable bladder, cystospasm, chronic or acute cystitis, prostatic hypertrophy or the like, or idiopathic pollakiuria, idiopathic urinary incontinence or the like.

The crystal polymorph related to the present invention can be used, if required, in combination with another medicament for the treatment of dysuria. Examples of such a medicament for the treatment of dysuria include anticholinergic agents such as oxybutynin hydrochloride, propiverine hydrochloride, tolterodine, darifenacin, fesoterodine, trospium chloride, KRP-197, YM-905 and the like; smooth muscle relaxants such as flavoxate hydrochloride and the like; $β_2$-adrenoceptor agonists such as clenbuterol hydrochloride, formoterol fumarate and the like; $α_1$-adrenoceptor agonists such as midodrine hydrochloride, R-450, GW-515524, ABT-866 and the like; estrogen preparations such as conjugated estrogen, estriol, estradiol and the like; central nervous system agents such as antiepileptic agents, antidepressants and the like such as imipramine, reserpine, diazepam, carbazepam and the like; neurokinin receptor antagonists such as TAK-637, SB-223956, AZD-5106 and the like; potassium channel openers such as capsaicin, resiniferatoxin and the like; vasopressin 2 receptor agonists such as desmopressin, OPC-51803, WAY-141608 and the like; $α_1$-adrenoceptor antagonists such as tamsulosin, urapidil, naftopidil, silodosin, terazosin, prazosin, alfuzosin, fiduxosin, AIO-8507L and the like; serotonin receptor antagonists such as REC-15-3079 and the like; dopamine receptor agonists such as L-dopa and the like, or dopamine receptor antagonists; antiallergic agents such as histamine receptor antagonists such as suplatast tosilate, norastemizole and the like; NO synthase inhibitors such as nitroflurbiprofen and the like.

These pharmaceutical compositions related to the present invention can be prepared by suitably admixing or by diluting and dissolving crystalline form F with appropriate pharmaceutical additives such as excipients, disintegrators, binders, lubricants, diluents, buffers, isotonicities, antiseptics, moistening agents, emulsifiers, stabilizing agents, dissolving aids and the like by pharmaceutically well-known method depending on the formulation.

In case of using a pharmaceutical composition comprising as an active ingredient the crystal polymorph of the present invention in the practical treatment, various dosage forms can be used depending upon their usages. As the dosage forms, for example, powders, granules, fine granules, dry syrups, tablets, capsules, injections, solutions, ointments, suppositories, poultices or the like can be illustrated, and they are orally or parenterally administered.

In case of using a pharmaceutical composition of the present invention in the practical treatment, the dosage of crystalline form C that is an active ingredient is appropriately decided depending on the age, sex, body weight and degree of symptoms and treatment of each patient, which is approximately within the range of from 0.01 to 100 mg per day per adult human in the case of oral administration and approximately within the range of from 0.003 to 30 mg per day per adult human in the case of parenteral administration, and the daily dose can be divided into one to several doses per day and administered suitably.

In case of uses of the crystal polymorph related to the present invention in combination with another medicament for the treatment of dysuria, pharmaceutical compositions can be formulated by admixing separately each of active ingredients, or admixing concurrently both of active ingredients, with pharmaceutically acceptable additives such as excipients, disintegrators, binders, lubricants, diluents, buffers, isotonicities, antiseptics, moistening agents, emulsifiers, stabilizing agents, dissolving aids and the like, and orally or pareterally administered. In case that pharmaceutical compositions are separately formulated, the compositions may be mixed together with an appropriate diluent and administered simultaneously. Alternatively, separately formulated pharmaceutical compositions may be administered separately, concurrently or at different intervals.

Effects of the Invention

Crystalline form F of the present invention is stable without causing chemical deterioration and polymorphic transformation under usual storage conditions, and the quality can be maintained constantly. In addition, crystalline form F is a crystal polymorph with superior water-solubility.

BEST MODE TO PUT THE INVENTION TO PRACTICE

Figure 1:
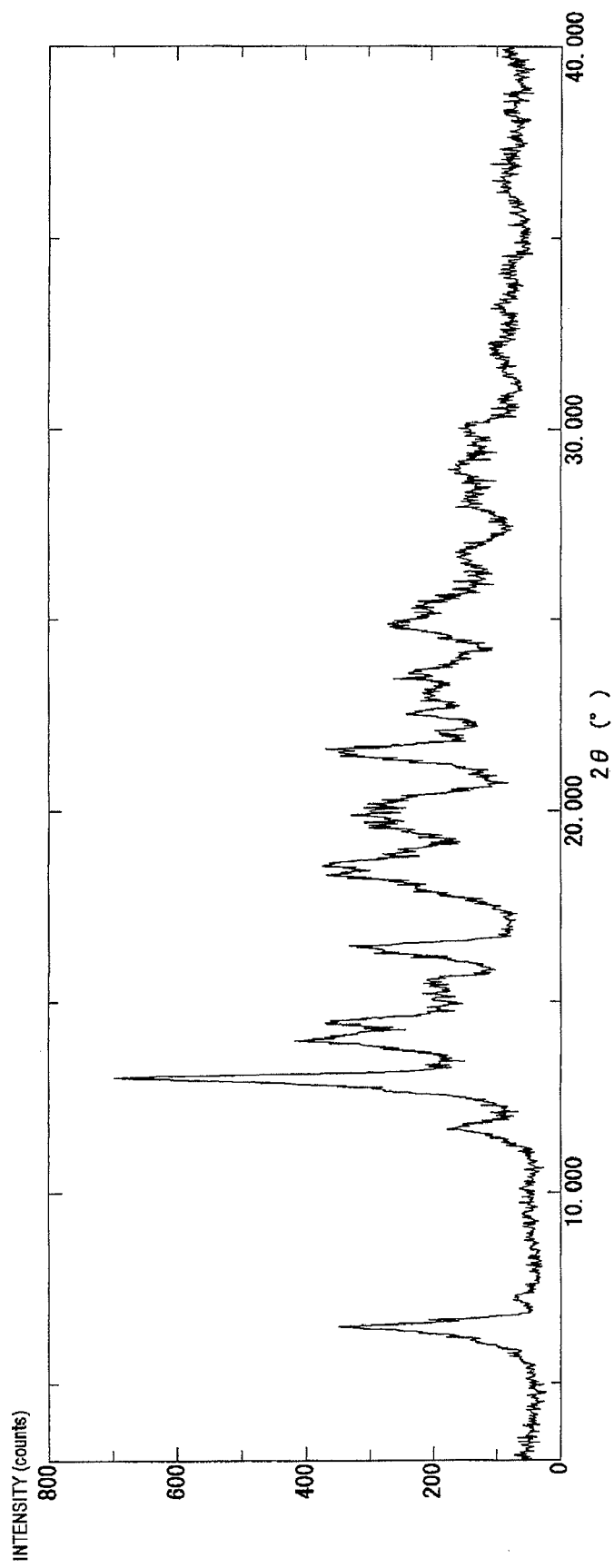
FIG. 1 shows the powder X-ray diffraction diagram of crystalline form F obtained in Example 1. The axis of ordinate shows the intensity of X-rays, and the axis of abscissa shows the angle of the diffraction (2θ).

The present invention is further illustrated in more detail by way of the following Test Examples. However, the present invention is not limited thereto.

The powder X-ray diffraction patterns of each crystal polymorph were measured by X-ray diffractometer RINT 2100 ultima+ manufactured by Rigaku Denki Corporation (measuring conditions; CuK α rays, 40 kV in X-ray tube voltage, 40 mA in X-ray tube current). The 2θ value of diffraction pattern by the powder X-ray diffractometry may deviate in some cases by a factor of about 0.5° depending on the sample conditions and measuring conditions. In addition, due to the properties of data, a total diffraction pattern of the powder X-ray diffractometry is important for the identification of crystals. The TG/DTA measurements of each crystal polymorph were conducted by thermogravimetry analyzer (TG/DTA) ThermoPlus 2 series TG8120 manufactured by Rigaku Denki Corporation (measuring conditions; temperature rising rate 10° C./minutes, samplepan (Al), reference ($Al_2O_3$), under a nitrogen atmosphere). Melting points of each crystal were searched from differential thermal analysis (DTA) endothermic peak (extrapolation). The solid state $^{13}$C-NMR spectrums of each crystal polymorph were measured by AVANCE/DRX500 manufactured by Bruker (measuring conditions; accumulated counts 512 times, contact time 3 msec, repeated time 5 sec, probe 4 mmMAS, observed frequency 125.77 Mhz, spinning rate 10000 Hz).

In addition, crystalline forms A and B of ethyl (−)-2-[4-[2-[[(1S,2R)-2-hydroxy-2-(4-hydroxyphenyl)-1-methylethyl]amino]-ethyl]-2,5-dimethylphenoxy]acetate hydrochloride were prepared by manufacturing methods described in Examples 2 and 3 in the above Patent Reference 2.

EXAMPLES

Example 1

Figure 3:
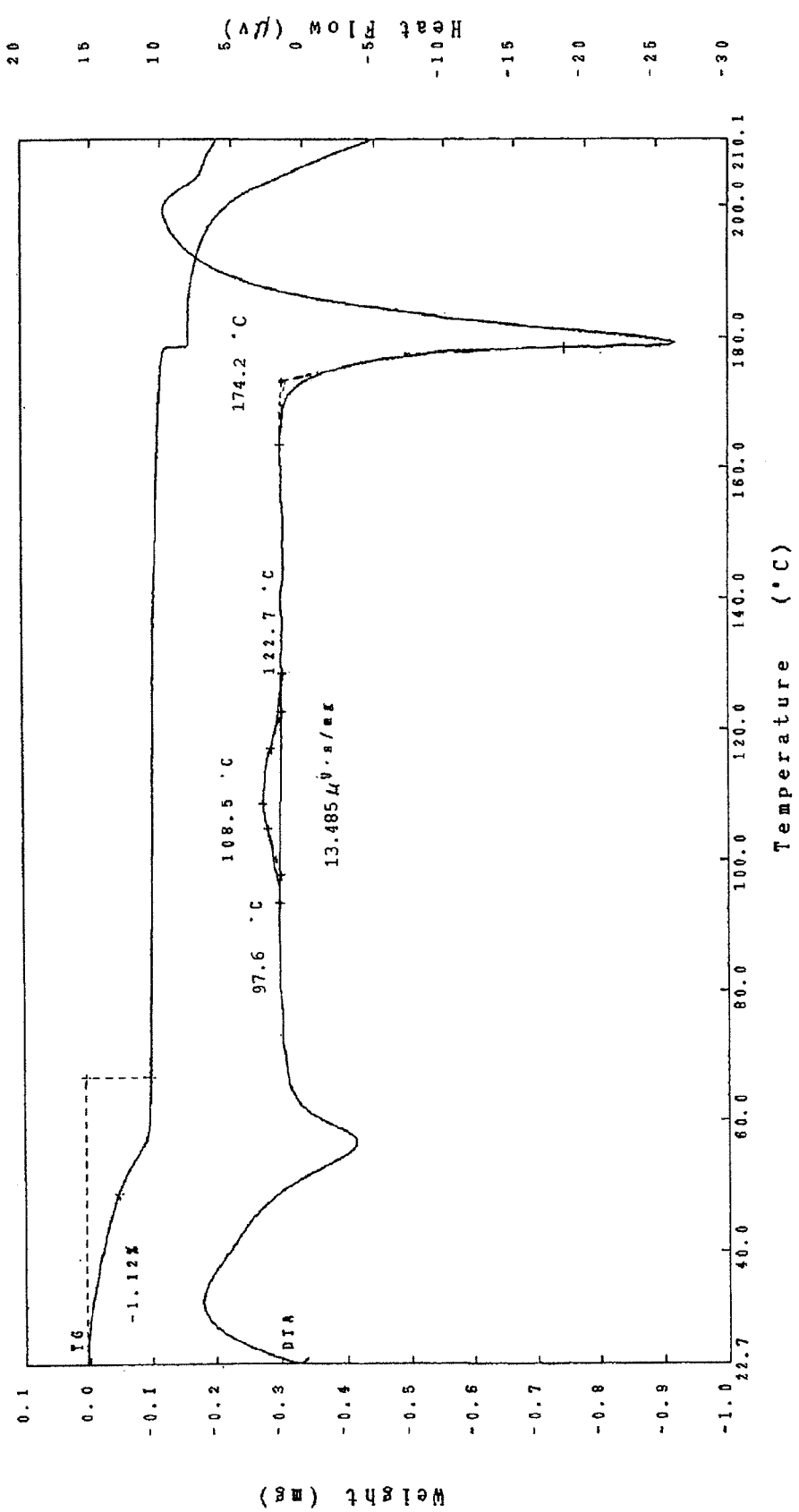
FIG. 3 shows TG/DTA measurements of crystalline form F obtained in Example 1 shown by the TG/DTA curves.
Figure 5:
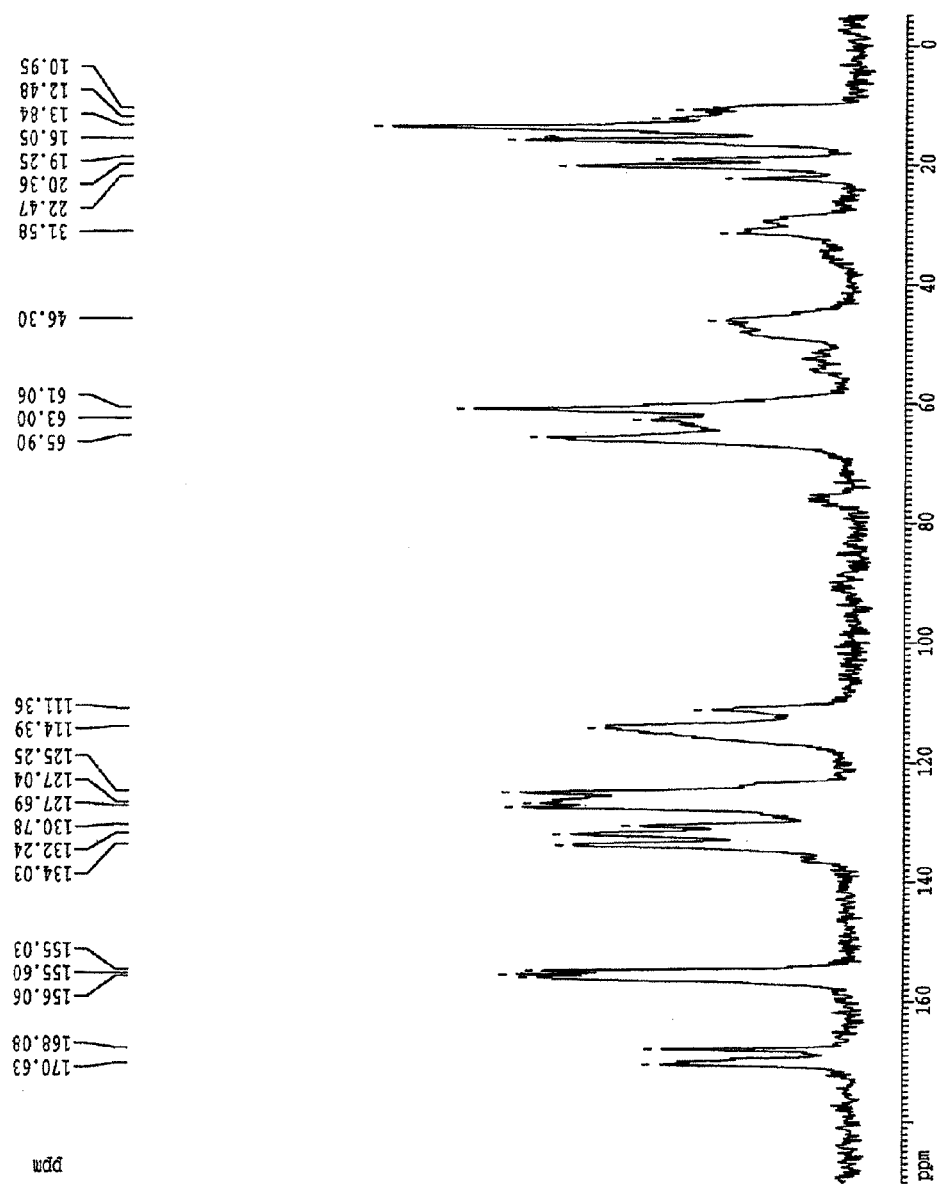
FIG. 5 shows solid state $^{13}$C-NMR spectrum of crystalline form F obtained in Example 1, the axis of abscissa shows chemical shifts (ppm).

Crystalline form F of ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride ¼ hydrate A mixture of ethyl 2-[4-(2-bromoethyl)-2,5-dimethylphenoxy]acetate (11.3 g), (1R,2S)-p-hydroxynorephedrine (5.0 g), diisopropylamine (4.54 g) and N,N-dimethylformamide (28 g) was stirred at 100° C. for 2 hrs under a nitrogen atmosphere. After cooling to room temperature, ethyl acetate (90 g) and water (38 g) were added to the reaction mixture. The organic layer was separated, and the aqueous layer was extracted with ethyl acetate (45 g). The combined organic layers were washed with water and brine successively, dried over anhydrous sodium sulfate. After the drying agent was separated by filtration, the solvent was removed under reduced pressure. Furthermore, the reaction mixture was heated to remove the solvent by azeotropy with toluene (20 g), and toluene (28.4 g) was added to the residue. To the resultant solution was added dropwise 30 weight % hydrogen chloride solution in ethanol (3.06 g) under ice cooling, and the resulting mixture was stirred at 20° C. for 2 hrs. The precipitated crystals were collected by filtration, dried at 60° C. in vacuo, and allowed to stand overnight at 25° C. and at 60% relative humidity to give 7.36 g of ethyl (−)-2-[4-[2-[[(1S, 2R)-2-hydroxy-2-(4-hydroxyphenyl)-1-methylethyl]amino]ethyl]-2,5-dimethylphenoxy]acetate hydrochloride ¼ hydrate. The crystals were measured by powder X-ray diffraction. The result is shown in FIG. 1. In addition, TG/DTA analysis (the result is shown in FIG. 3) was measured and solid state $^{13}$C-NMR spectrum (the result is shown in FIG. 5) was also measured. The equivalents of hydrate were determined by direct titration of volumetric titration method of Karl-Fisher method.

Diffraction angles (2θ): 6.5, 11.7, 13.0, 14.0, 16.4, 18.6 and 21.6

Melting point: 174 to 178° C.

Reference Example 1

Ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride (Compound III)

A suspension of ethyl 2-[4-(2-ethoxy-2-hydroxyethyl)-2,5-dimethylphenoxy]acetate (68.7 g), 10% palladium carbon (50% wet, 17 g), (1R,2S)-2-amino-1-(4-hydroxyphenyl)propan-1-ol (38.0 g) and tetrahydrofuran (380 g) was stirred under a hydrogen atmosphere at 40° C. for 5 hours. After the catalyst was removed by filtration, the filtrate was concentrated under reduced pressure. The residue was dissolved in toluene, and washed with water, an aqueous solution of sodium bicarbonate and brine successively. The organic layer was dried over anhydrous sodium sulfate, and the solvent was removed under reduced pressure. To the residue was added toluene (200 g) and ethanol (21 g), and 20 weight % hydrogen chloride in ethanol (37.3 g) was added dropwise. The precipitated crystals were collected by filtration to give white crystal of ethyl (−)-2-[4-[2-[[(1S,2R)-2-hydroxy-2-(4-hydroxyphenyl)-1-methylethyl]amino]ethyl]-2,5-dimethylphenoxy]-acetate hydrochloride (70.2 g).

1H-NMR (DMSO-d6) δ ppm: 0.96 (3H, d, J=6.6 Hz), 1.21 (3H, t, J=7.1 Hz), 2.15 (3H, s), 2.25 (3H, s), 2.8-3.2 (4H, m), 4.16 (2H, q, J=7.1 Hz), 4.76 (2H, s), 4.9-5.1 (1H, m), 5.8-6.0 (1H, s), 6.68 (1H, s), 6.76 (2H, d, J=8.5 Hz), 6.96 (1H, s), 7.17 (2H, d, J=8.5 Hz), 8.5-9.0 (2H, br), 9.41 (1H, s)

Reference Example 2

Figure 2:
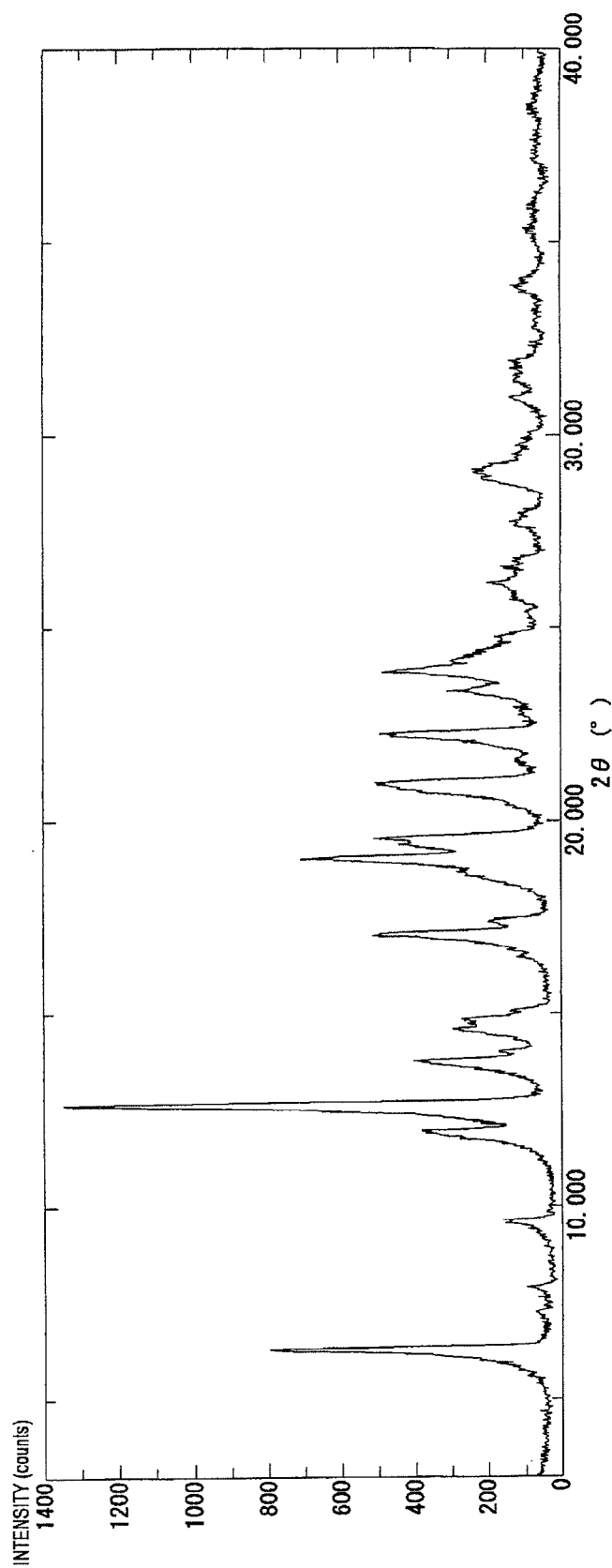
FIG. 2 shows the powder X-ray diffraction diagram of crystalline form G obtained in Reference Example 1. The axis of ordinate shows the intensity of X-rays, and the axis of abscissa shows the angle of the diffraction (2θ).
Figure 4:
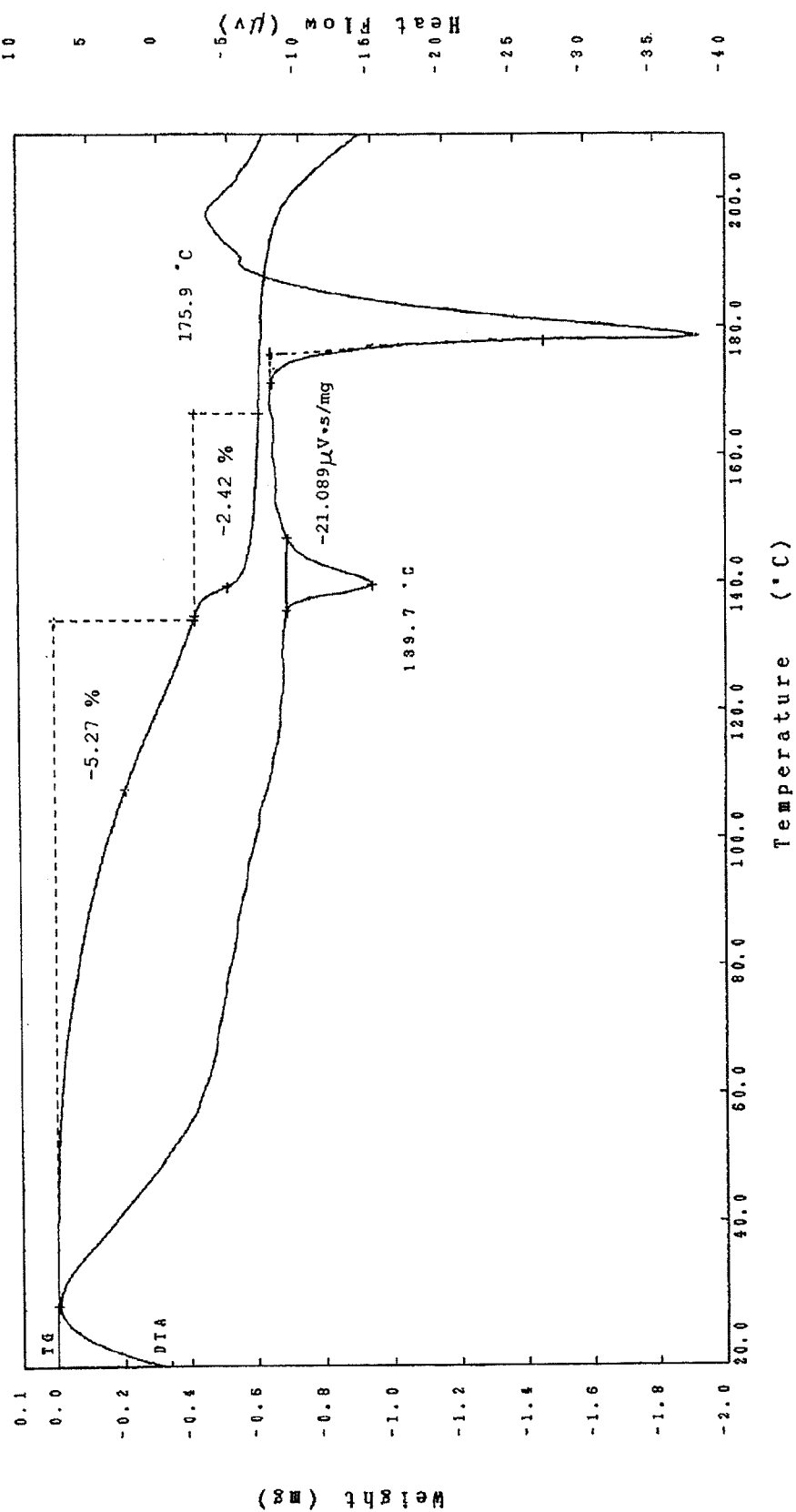
FIG. 4 shows TG/DTA measurements of crystalline form G obtained in Reference Example 1 shown by the TG/DTA curves.
Figure 6:
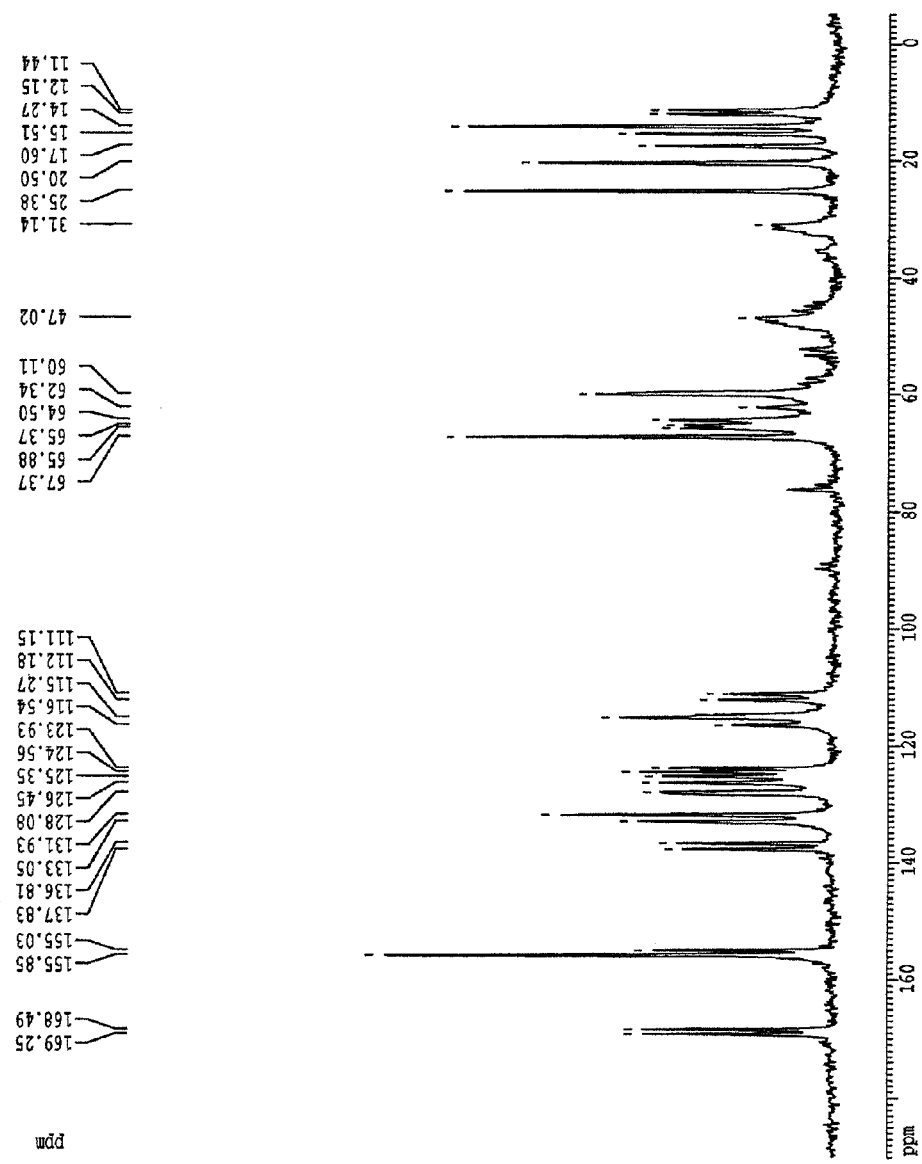
FIG. 6 shows solid state $^{13}$C-NMR spectrum of crystalline form G obtained in Reference Example 1, the axis of abscissa shows chemical shifts (ppm).

Crystalline form G of ethyl (−)-2-[4-[2-[[(1S,2R)-2-hydroxy-2-(4-hydroxyphenyl)-1-methylethyl]amino]ethyl]-2,5-dimethylphenoxy]-acetate hydrochloride ½ tetrahydrofuran solvate A mixture of compound (III) (1 g) obtained in Reference Example 1, methanol (2 mL), and tetrahydrofuran (10 mL) were stirred under heating condition to dissolve. To the solution tetrahydrofuran (10 mL) was added to dissolve and the solution was concentrated by heating at normal pressure (the volume of the distilled solvent was 14 g). After cooling, the precipitated crystals were collected by filtration and dried in vacuo at room temperature. The obtained crystals were analyzed by powder X-ray diffraction, and the result is shown in FIG. 2. In addition, equivalents of tetrahydrofuran were calculated based on the TG/DTA analysis (the result was shown in FIG. 4) and assay by gas chromatography. The solid $^{13}$C-NMR spectrum was also measured (the result is shown in FIG. 6).

Diffraction angles (2θ): 6.3, 11.9, 12.6, 17.0, 19.0, 20.9 and 22.2

Melting point: 174 to 178° C.

Reference Example 3

Amorphous form of ethyl (−)-2-[4-[2-[[(1S,2R)-2-hydroxy-2-(4-hydroxyphenyl)-1-methylethyl]amino]ethyl]-2,5-dimethylphenoxy]acetate hydrochloride Compound (III) (1 g) obtained in Reference Example 1 was dissolved in water (260 mL). After the solution was frozen in dry-ice acetone bath, the frozen solution was freeze-dried under reduced pressure to give the title amorphous form.

Test Example 1

Solubility Test

Each crystal polymorph (0.4 g), which was prepared by the above method, was taken in 50 mL Erlenmeyer flask respectively, and to the mixture was added 20 mL of the mediums as defined below. The flask was shaken at 125 strokes per minute at 37° C. After 0.5, 1, 2 and 20 hours from the start of shaking, 1.5 mL of the suspension was filtered through a membrane filter (pore size: 0.2 μm). The concentration of the filtrate for each crystal polymorph was determined by HPLC method to determine the solubility. The concentration where the concentration became constant by the temporal measurements of the concentration was determined to be the solubility of each polymorph, and the results are shown in Table 1. When the maximum value was observed in the course of measurement, the maximum value was determined to be the solubility. In the cases of crystalline form F and amorphous form, since these samples were dissolved completely in each medium within 0.5 hours after the start of the test, additional samples were added appropriately to the test flasks at the point of 0.5 hours after the start and the solubility tests were continued.

The mediums: water or the first fluid of disintegration test of Japanese Pharmacopoeia (hereinafter referred to as The First Fluid).

As the results were shown in Table 1, the solubility of crystalline form F of the present invention in water was about 1.4 to 2.3 times as high as those of crystalline forms A and B and amorphous form. Furthermore, the solubility of crystalline form F in The First Fluid was about 5 times as high as those of them.

TABLE 1

| crystal form | water (mg/mL) | The First Fluid (mg/mL) |
| --- | --- | --- |
| crystal form F | 24.3 | 11.8 |
| crystal form A | 10.7 | 2.4 |
| crystal form B | 12.5 | 2.9 |
| amorphous form | 17.8 | 2.6 |

Test Example 2

Chemical Stability Test

Crystalline form F obtained in Example 1 was stored at 60° C. for 1 week to investigate the chemical stability. As the chemical stability, the residual percentage of ethyl (−)-2-[4-[2-[[(1S,2R)-2-hydroxy-2-(4-hydroxyphenyl)-1-methylethyl]amino]ethyl]-2,5-dimethylphenoxy]-acetate was determined by HPLC, and the change in appearance was also observed. The results are also shown in Table 2.

As shown in Table 2, crystalline form F of the present invention indicates no changes in both of chemical purity and appearance, and has an excellent storage stability.

TABLE 2

| storage period | crystal form F | |
| --- | --- | --- |
|  | at start | after 1 week |
| residual percentage (chemical purity %) | 98.1 | 98.1 |
| appearance | white | white |

INDUSTRIAL APPLICABILITY

Since crystalline form F of the present invention has an excellent storage stability, it is stable over long periods under the usual storage condition (25° C. and 60% relative humidity) and can be provided as medicinal bulks with the constant crystalline form maintained in quality. In addition, crystalline form F is useful as a medicine because of the superior water-solubility.

The invention claimed is:

1. Solid ethyl (−)-2-[4-[2-[[1S,2R]-2-hydroxy-2-(4-hydroxy-phenyl)-1-methylethyl]amino]ethyl]-2,5-dimethylphenoxyacetate hydrochloride ¼ hydrate having a powder X-ray diffraction pattern with characteristic peaks at diffraction angels ($2\theta$) of 6.5, 11.7, 13.0, 14.0, 16.4, 18.6 and 21.6.

2. A pharmaceutical composition comprising as an active ingredient a compound as claimed in claim 1.

3. An agent for treating pollakiuria or urinary incontinence, comprising as an active ingredient a compound as claimed in claim 1.

\* \* \* \* \*